United States Patent [19]

Cardone et al.

[11] Patent Number: 5,573,957
[45] Date of Patent: Nov. 12, 1996

[54] MONOCLONAL ANTIBODY TO HUMAN CARDIAC MYOGLOBIN

[75] Inventors: Beatrice Cardone, Etobicoke; George Jackowski, Inglewood, both of Canada

[73] Assignee: Spectral Diagnostics, Inc., Toronto, Canada

[21] Appl. No.: 314,044

[22] Filed: Sep. 28, 1994

[51] Int. Cl.$^6$ .................................................. G01N 33/553
[52] U.S. Cl. ........................ 436/518; 435/7.92; 435/7.94; 435/7.95; 435/240.26; 436/531; 436/548; 436/66; 436/811; 530/388.1; 530/388.2; 530/388.25; 530/389.1; 530/389.3; 530/391.1; 530/809; 530/841
[58] Field of Search .................................. 435/7.92, 7.94, 435/7.95, 240.26; 436/518, 531, 548, 66, 811; 530/388.1, 388.2, 388.25, 389.1, 389.3, 391.1, 809, 841

[56] References Cited

U.S. PATENT DOCUMENTS 5,290,678  3/1994  Jackowski .............................. 435/7.4

OTHER PUBLICATIONS

Borrebaeck, C. A. K. (1983) Scand. J. Immunol., 18:9–12.
East, I. J. et al. (1981) J. Biol. Chem., 257:3199–202.
Hurrell, J. G. R. et al. (1981) J. Immunol. Methods, 45:249–54.
Moscoso, H. et al. (1990) J. Clin. Lab. Anal., 4:437–42.
H. Pfund et al, "The Conformation Sensitive Immunoassay . . . " in Molecular Immunology, 27(6):495–502, 1990.
M. Shields et al, "An appraisal of polystyrene–(ELISA) and nitrocellulose–based (ELIFA) enzyme immunoassay . . . " in J. of Immunol. Methods, 141(1):253–261, 1991.
C. Schwab et al, "Coveats for the use of surface–adsorbed protein antigen to test the specificity of antibodies," in J. of Immunol. Methods, 147(1):125–134, 1992.
J. Smith et al, "Conformational Integrity of Myoglobin after Immunization with Freund's Adjuvant," in J. of Immunology, 118(1):226–228, 1977.
B. Johne et al, "Epitope mapping and binding kinetics of monoclonal antibodies studied by real time biospecific interaction . . . " in J. of Immunol. Methods 160(2):191–198, 1993.
E. Juronen et al., "Rapid, simple and sensitive antigen capture ELISA for the quantitation of myoglobin . . . " in J. of Immunol. Methods 111(1):109–115, 1988.
J. Harrell et al., "Immunological Measurements of Conformational Motility in Regions of the Myoglobin Molecule", Biochemistry 16(2):175–185, 1977.

Primary Examiner—Carol A. Spiegel
Attorney, Agent, or Firm—Klauber & Jackson

[57] ABSTRACT

A monoclonal antibody having high affinity to human cardiac myoglobin, which has undergone a conformational change resulting from the binding of the molecule to another molecule is described. This monoclonal antibody can be used in a rapid format double antibody immunoassay system to identify blood, serum or plasma levels of cardiac myoglobin. Such an immunoassay system can be used for diagnosing and quantifying myocardial necrosis and infarction.

4 Claims, 6 Drawing Sheets

MONOCLONAL ANTIBODY TO HUMAN CARDIAC MYOGLOBIN

FIELD OF INVENTION

This invention relates to a monoclonal antibody which demonstrate specific binding to human cardiac myoglobin. More specifically, this invention relates to a monoclonal antibody that recognizes an epitope of the myoglobin molecule that is only exposed as a result of having undergone a conformational change resulting from the binding of the molecule to another molecule. The present invention also relates to the hybridoma cell line, designated as 5Mb-64, and the monoclonal antibody produced by the same. The present invention further relates to a diagnostic system using the monoclonal antibody from the hybridoma cell line 5Mb-64, as an antibody in a sandwich assay to detect blond, serum or plasma levels of myoglobin. The antibody is particularly useful in a rapid format assay system.

BACKGROUND AND PRIOR ART

Myoglobin is one of the major proteins in skeletal and cardiac muscle. This oxygen binding lieme protein is comprised of a single polypeptide chain with a reported molecular weight of 17.8 kDa. Myoglobin's tertiary structure has been extensively studied, and it is reported that 75% or the main chain is folded in an alpha helical conformation (Edmundson A. B., Biochem. Prop. 1968; 12, 41–52; Kagen L. J. (1973) In: F. Borek (Ed.), Myoglobin, Biochemical, Physiological, and Clinical Aspects. Columbia University Press, New York).

Although its precise physiological function remains controversial, it is known that its ability to combine reversibly to oxygen is reflective of its role in oxygen transport to the muscle cell. Normal human myoglobin levels in the blood range from 0 to 70 ng/ml.

Following muscle injury, both cardiac and skeletal serum levels of myoglobin are dramatically increased. Reflective of its small molecular size, myoglobin is able to translocate into the vascular system without processing in the lymphatic system. In certain health disorders and/or diseases serum myoglobin is known to be elevated. This elevation is thought to be caused by the release of myoglobin from damaged or necrotic muscle cells.

Acute Myocardial Infarction (AMI) affects millions of people each year, many of whom die because diagnosis or treatment was not available in time to save their lives. Studies have shown that if a correct diagnosis of AMI, and appropriate therapeutic intervention is performed within the first 6 hours after the onset of chest pain, the chances of survival are greatly increased. Thus, the goal of medical investigators has been to develop an analytical system which will identity those early indicators of this condition. In MI patients, blood, serum and plasma cardiac myoglobin levels are known to be above normal as early as 30 minutes after the onset of chest pain. In fact, in some MI patients, cardiac myoglobin levels may increased by 10 fold of that of a normal person over the course of the MI. Myoglobin is said to display a temporal release into the circulation. In MI patients, myoglobin levels may rise above normal within 2 hours, will reach peak serum levels in 6–9 hours, and will return back to normal levels by 24 to 36 hours after the onset of chest pain (Vaidya H. C., Laboratory Medicine, 1992; 23:306–310). Thus monitoring the rapid release of cardiac myoglobin can be used as an indicator of MI.

MI patients in the early stages of the disease (under 6 hours) are most often administered reperfusion treatment with streptokinase or TPA (tissue plasminogen activator) These thrombolytic agents act to restore blood flow in the occluded vessels. The serial measurement of myoglobin has proven useful in the monitoring of such treatments, since myoglobin levels peak approximately 45 minutes after successful reperfusion (Bllis A. K., et, al, Circulation, 1985; 72:639–647).

Several detection methods for myoglobin have been established, but each method has limitations which directly affect its clinical utility. The need for a non-invasive method of myoglobin detection was realized more than 25 years ago, and the earliest tests developed were radioimmunoassay (Stone M. J., et. al., J. Clin Invest., 1975; 56:1334–1339). In these assays the serum sample was combined with a radiolabelled myoglobin and an anti-myoglobin polyclonal antibody. The antibody was then precipitated with a second radiolabelled polyclonal antibody. The concentration of myoglobin in the sample was calculated based on the inverse of the amount of precipitated radioactivity. This method was limited as it required extremely skilled technicians, was time consuming and posed a radiation risk.

The latex agglutination method of myoglobin detection utilizes monoclonal antibodies directed to myoglobin, which have been immobilized on later particles (Chapelle J. P., et al. Clin. Chim. Acta. 1985; 145:143–150). These monoclonal antibodies combinc with serum myoglobin and form aggregates. The quantification of the aggregation is proportional to the myoglobin concentration. This assay is more rapid and practical than the RIA, but only semi-qualitative results are produced. This method was recently adapted into both the turbidometric (Turbitimer, Behring, Germany, Tuengler P., et al., Behring Inst. Mitt., 1988; 82:282–308) and the immunonephelometric system (NA Latex Myoglobin, Behring, Germany, Massoubre, C., Clin. Chim. Acta., 1991; 201:223–230). Both of these methods report low intra- and inter-assay variation. These methodologies are limited however, because of the analytical time required, inadequate specificity and the need for expensive analyzers.

Therefore, there remains a need for a monoclonal antibody that demonstrates high affinity and specificity for human myoglobin that can be used as a reagent in an immunoassay system to identity blood, serum or plasma levels of myoglobin in patients with cardiac muscle damage (e.g. myocardial infarction). Such an immunoassay system, can be used for diagnosing and quantifying myocardial necrosis and infarction according to the rapid format procedure disclosed in U.S. Pat. No. 5,290,678.

SUMMARY OF THE INVENTION

The limitations of the prior art are addressed in the present invention by providing a monoclonal antibody that is specific for and has high affinity for human cardiac myoglobin. Specifically the present invention relates to a monoclonal antibody which recognizes a unique epitope or region of human cardiac myoglobin which is only exposed as a result of the myoglobin molecule having undergone a conformational change resulting from the binding to another molecule, for example, an antibody. This monoclonal antibody can be used in the rapid and specific identification of the myoglobin protein in human blood, serum or plasma.

Thus according to the present invention there is provided a monoclonal antibody, which recognize an epitope of human cardiac myoglobin, which is only exposed as a result of the myoglobin molecule having undergone a conformational change resulting from the binding to another molecule.

Further according to the present invention, there is provided a hybridoma cell line producing said monoclonal antibody. In this embodiment, the hybridoma cell line is 5Mb64, deposited with American Type Culture Collection 12301 Parklawn Drive, Rockville, Md. USA on Aug. 25, 1994 under Accession Number HB 11708.

According to a further embodiment of the preset invention, there is provided a method of detecting myoglobin in a sample using a monoclonal antibody produced from hybridoma cell line 5MB64, deposited with American Type Culture Collection under Accession Number HB 11708, which comprises contacting the sample with an anti-myoglobin rabbit polyclonal antibody to produce a polyclonal antibody myoglobin complex; contacting the complex with the monoclonal antibody to produce a polyclonal antibody-myoglobin-monoclonal antibody complex; and detecting the polyclonal antibody-myoglobin-monoclonal antibody complex.

DETAILED DESCRIPTION OF THE INVENTION

The monoclonal antibody of the present invention can be distinguished from the antibodies known in the art in terms of its diagnostic value due to its specificity, sensitivity and high affinity for human cardiac myoglobin.

Antibodies employed to achieve high sensitivity in diagnostic immunoassays must have both high affinity for the antigen and good binding kineties. As optimal interactions of monoclonal antibodies with antigens are essential to achieve required levels of sensitivity, the selection system is crucial to the assay's success. However the immunoactivity of monoclonal antibodies can be dramatically altered when coupled to a matrix or conjugated to a label molecule. Likewise, the bond formed between an antibody and its corresponding antigen may in fact result in the antigen having undergone a conformational change or stoichiometric rearrangement. This conformational change will greatly affect the ability or a second antibody to bind to the antigen. This stoichiometric hindrance or enhancement, when identified, can greatly affect the success or failure of the assay sensitivity (Johne B., et al., J. Immunol. Methods, 1993, 160:191–198). The monoclonal antibody of the present invention was only able to bind the antigen, myoglobin, if the structure of the molecule had been changed as a result of binding to another molecule. According to the examples of the present invention, this conformational change can result from the binding of the myoglobin to a polystyrene plate or to an anti-myoglobin rabbit polyclonal antibody. Immunoactivity of the monoclonal antibody of the present invention was enhanced when the myoglobin was first bound to an anti-rabbit polyclonal antibody.

In the conventional ELISA a capture antibody is coated onto a microtitre plate, or other solid support matrix. To this solid support-capture antibody complex is added an antigen, which is then followed by a detector antibody, which is labelled. It is the label molecule on the detector antibody which allows the antibody-antigen interaction to be visualized. Thus, in this embodiment, the monoclonal antibody of the present invention is a detector antibody, which recognizes an epitope of myoglobin that is only exposed as the result of a conformational change in the molecule resulting from the binding of the molecule to a first antibody (capture antibody).In this embodiment the anti-myoglobin rabbit polyclonal antibody caused this conformational change in the myoglobin molecule when the myoglobin molecule bound to the polyclonal antibody.

Polyclonal antibodies prepared against myoglobin can be prepared using known procedures. A typical protocol would employ 5 to 6 large animals, such as rabbits, sheep or goats injected either in the footpads, for rabbits or intramuscularly into multiple sites with about 1 to 5 mg in complete Freund's adjuvant in a total volume of 0.25 to 0.5 ml. With smaller animals, such as mice and guinea pigs, microgram amounts (1 to 100 µg in 0.02 to 2.0 ml) are Injected in the footpads subcutaneously or intraperitoneally. The animals are bled weekly for 4 to 6 weeks beginning about 3 weeks after the immunization. The sera is separated and tested for the production of antibody. Rabbits and larger animals can be bled from the rear vein or via jugular vein puncture. With mice sera can be obtained via retroorbital trappings of blood. Booster injections are given, as required. In general high affinity antibody follows immunization with low doses of antigen, and the best sera in rabbits can be obtained about 3 to 5 months after immunization There are several methods of evaluating and analyzing antibody-antigen interactions. The most commonly used and accepted methods include the Half Sandwich ELISA (Enzyme Linked Immunosorbent Assay) the Full Sandwich ELISA and the Immunoblot. Recently a new analytical tool has been introduced which permits the investigator to observe the antibody-antigen association in a practical and useful time frame. The BIAcore™ system (Biospecific Interaction Analysts System, Pharmacia Biosensor, Piscataway, N.J.) is a biosensor that utilizes the quantum mechanical phenomenon of Surface Plasmon Resonance (SPR) to detect and analyze the interactions of biological molecules. Biological reactants (eg. antibodies or antigens) are covalently attached to a dextran matrix lying on the surface of a gold/glass sensor chip interface. Near infra red light, directed onto the opposite side of the sensor chip surface, is reflected, and also induces an evanescent wave in the gold film, which in turn causes an intensity dip in the reflected light at a particular angle known as the resonance angle. If the refractive index of the sensor chip surface is altered (e.g. by antigen binding to antibody) a shift occurs in the resonance angle. This angle shift can be measured and is expressed as resonance units (RUs) such that 1000 RUs is equivalent to a change in surface protein concentration of 1 ng/mm². These changes are recorded on a sensorgram which depicts the association and dissociation of any biological reaction (in this case antibodies and antigens)

The monoclonal antibody of the present invention was prepared by conventional procedures, generally following the methods of Kohlers and Milstein (Nature, 256, 495–497, 1975; Eur. J. Immunol. 6, 511–519, 1976). According to this method, tissue culture adapted mouse myeloma cells are fused to antibody producing cells from immunized mice to obtain the hybrid cells that produce large amounts of a single antibody molecule. In general, the antibody producing cells are prepared by immunizing an animal, for example, mouse, rat, rabbit, sheep, horse, or bovine, with an antigen. The immunization schedule and the concentration of the antigen in suspension is such as to provide useful quantities of suitably primed antibody producing cells. These antibody producing cells can be either spleen cells, thymocytes, lymph node cells and/or peripheral blood lymphocytes.

The antibody producing cells are then fused with myeloma cells, cell lines originating from various animals such as mice, rats, rabbits, and humans, can be used, using a suitable fusion promoter. Many mouse myeloma cell lines are known and available generally from members of the academic community and various depositories, such us the American Type Culture Collection, Rockville, Md. The myeloma cell line used should preferably be medium sensitive so that unfused myeloma cells will not survive in a selective media, while hybrids will survive. The cell line most commonly used is an 8-azaguanine resistant cell line, which lacks the enzyme hypozanthine-guanine-phosphoribosyol-transferase and therefore will not be supported by HAT. (hypoxanthine-aminopterin-thymidine) medium. In general, the cell line is also preferably a "non-secretor" type, in that it does not produce any antibody. The preferred fusion promoter is polyethyleneglycol having an average molecular weight from about 1000 to about 4000. Other fusion promoters such as polyvinylalcohol, a virus or an electrical field can also be used.

The immortalized cells (hybridoma) must then be screened for those which secrete antibody of the correct specificity. The initial screening is generally carried out sing an enzyme-linked immunosorbent assay (ELISA). Specifically the hybridoma culture supernatants are added to microtitre plates which have been previously coated with the antigen, in this case myoglobin. A bound specific antibody from the culture supernatants can be detected using a labelled second antibody, for example, goat anti-mouse IgG labelled with peroxidase (commercially available).Cultures that are positive against the antigen are then subjected to cloning by the limiting dilution method. Secondary hybridoma cultures are re-screened as described above, and further positive cultures are then examined using the BIAcore system (Pharmacia Biosensor AB, Uppsala, Sweden). The cultures are then evaluated as to determine whether or not the antibody binds the antigen and to determine the kinetic profile of antigen binding. A selected culture based on these results is subject to further cloning until culture stability and clonality are obtained. Immediately after hybridization, the fusion products will have approximately 80 chromosomes, and as these cells proceed to divide they will randomly lose some of these chromosomes. The cloning process is to select those cells which still have the chromosomes coding for antibody production. The cloning process is repeated until 100% of the subpopulation exhibits the production of a specific antibody, which is indicative of the "stability" of the hybridoma. In addition, hybridoma culture wells often have multiple colonies some of which may be antibody non-producers. The cloning process allows the selection of a positive hybrid which is derived from a single cell.

The monoclonal antibody of the present invention can be produced either using a bioreactor or from ascites, both procedures of which are well known in the art The monoclonal antibody of the present invention can be used in an immunoassay system for determining blood, serum or plasma levels of myoglobin.

Current immunoassays utilize a double antibody method for detecting the presence of an analyte. These techniques are reviewed in "Rasie Principals of Antigen-Antibody Reaction", Elvin A. Labat, (Methods in Enzymology, 70, 3–70, 1980). Such Systems are often referred to as fast format systems because they are adapted to rapid determinations of the presence of an analyte. The system requires high affinity between the antibody and the analyte. According to one embodiment ofthe present invention, the presence of cardiac myoglobin is determined using a pair of antibodies, each specific for myoglobin and at least one antibody specific for cardiac myoglobin. One of said pairs of antibodies is referred to herein as a "detector antibody" and the other of said pair of antibodies is referred to herein as a "capture antibody". The monoclonal antibody of the present invention can be used as a detector antibody, wherein the myoglobin has already been bound by a capture antibody. One embodiment of the present invention thus uses the double antibody sandwich method for detecting cardiac myoglobin in a sample of biological fluid. In this method, the analyte (cardiac myoglobin) is sandwiched between the detector antibody and the capture antibody, the capture antibody being irreversibly immobilized onto a solid support. The detector antibody would contain a detectable label, in order to identify the presence of the antibody-analyte-antibody sandwich and thus the presence of the analyte.

Common early forms of solid supports were plates, tubes or beads or polystyrene which are well known in the field of radioimmunoassay And enzyme immunoassay. More recently, a number or porous material such as nylon, nitrocellulose, cellulose acetate, glass fibers and other porous polymers have been employed as solid supports.

One embodiment of the present invention uses a flow-through type immunoassay device. Valkirs et al. (U.S. Pat. No. 4,632,901) disclose a device comprising an antibody, specific to an antigen analyte, bound to a porous membrane or filter to which is added a liquid sample. As the liquid flows through the membrane, target analytes bind to the antibody. The addition of the sample is followed by the addition of a labelled antibody. The visual detection of the labelled antibody provides an indication of the presence of the target analyte in the sample.

Another example of a flow-through device is disclosed in Kromer et al. (EP-A 0 229 359). which described a reagent delivery system comprising a matrix saturated with a reagent or components thereof dispersed in a water soluble polymer for controlling the dissolution rate of the reagent for delivery to a reaction matrix positioned below the matrix In migration type assays, a membrane is impregnated with the reagents needed to perform the assay. Au analyte detection zone is provided in which labelled analyte is bound and assay indicia is read. For example, see Tom et al. (U.S. Pat. No. 4,366,241), and Zuk (EP-A 0 143 574). Migration assay devices usually incorporate within them reagents which have been attached to coloured labels thereby permitting visible detection of the assay results without the addition of further substances. See for example Bernstein (U.S. Pat. No. 4,770,853), May et al. (WO 88/08534), and Ching et al. (EP-A 0 299 428). The monoclonal antibody of the present invention can be used in all of these known types of flow-through devices.

Direct labels are one example of labels which can be used according to the present invention. A direct label has been defined as an entity, which in its natural stare, is readily visible, either to the naked eye, or with the aid of In optical filter and/or applied stimulation, e.g. U.V. light to promote fluorescence. Among examples of coloured labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such a described by May, supra, Snyder (EP-A 0 280 559 and 0 281 327); or dyes encapsulated in liposomes as described by Campbell et, al. (U.S. Pat. No. 4,703, 017).Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6 phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Other examples of biological diagnostic devices, which can be used for the detection of cardiac myoglobin, using the monoclonal antibody of the present invention, include the devices described by G. Grenner, P. B. Diagnostics Systems, Inc., in U.S. Pat. No. 4,906,439 and 4,918,025.

In one embodiment of the present invention the diagnostic test uses a blood sample tube which is commonly used to draw blood samples from patients. The inside wall of the tube acts as a carrier for the monoclonal or polyclonal antibodies and required reagents or detection means, needed to produce a measurable signal. In this embodiment the capture antibody is immobilized onto the wall of the test tube. After the sample is drawn from the patient, the user simply shakes the sample with the detector antibody in the tube so that the detector antibody reacts with any cardiac myoglobin in the blood. In this example the monoclonal antibody of the present invention is the detector antibody. It may be necessary to use a sample wherein the red blood cells have been removed, so that the red blood cells will not interfere with the analysis of the results. If the analyte is present in the blood, it will be sandwiched between the capture antibody and the detector antibody which contains a suitable label for direct detection or reacts with the reagents in an indirect assay. The solid support (the test rube) can then be rinsed free of unbound labelled material. A variety of solid supports can be used according to this method, for example, test tube walls, plastic cups, bends, plastic balls and cylinders including microtitre plates, paper, and glass fibers.

There are currently available several types of automated assay apparatus which can undertake rapid format assays on a number of samples contemporaneously. These automated assay apparatus include continuous/random access assay apparatus. Examples of such systems include OPUS™ of PB Diagnostic System, Inc. and the IMC™ Analyzer introduced by Abbott Laboratories of North Chicago, Ill., in 1988. In general, a sample of the test fluid is typically provided in a sample cup and all the process steps including pipetting of the sample into the say test element, incubation and reading of the signal obtained are carried out automatically. The automated assay systems generally include a series of work stations each of which performs one of the steps in the test procedure. The assay element may be transported from one work station to the next by various means such as a carousel or movable rack to enable the test steps to be accomplished sequentially. The array elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps. typically a fluorescent or a colorimetric change in the reagents present on the porous member to be read, such as by means of a spectroscopy or fluorometer which are included within the assay system.

The automated assay say instruments of PB Diagnostic Systems, Inc. are described in U.S. Pat. Nos. 5,051,237; 5,138,868; 5,141,871 and 5,147,609.

A description of the IMX Analyzer is included in the "Abbott IMX Automated Bench Top Immunochemistry Analyzer System" by Fiore, M. et al., *Clinical Chemistry*, 35, No. 9, 1988. A further example of these analyzers has been described in U.S. Pat. No. 4,956,148 entitled "Locking Rack and Disposable Sample Cartridge" issued to C. J. Grandone on Sep. 1, 1990, and assigned to Abbott Laboratories, which describes a carousel for carrying a plurality of reaction cells for use in connection with the Abbott IMX™ system. A further development in the art has been described in Canadian Patent Application 2,069,531, Chadwick M. Dunn et al., assigned to Abbott Laboratories wherein the immunochemistry analyzer system, described in this prior art application, has the capability of testing for up to three or four analytes in a single batch during a single run using currently available instrumentation. The system described in the Canadian application referred to above enables the users to group three small batches of assays together rather than run three separate analyses. The monoclonal antibody of the present invention can be used in these automated analyzers.

A further class of immunochemical analyzer Systems, in which the monoclonal antibody of the present invention can be used, are the biosensors or optical immunosensor systems. In general an optical biosensor is a device which uses optical principles quantitatively to convert chemical or biochemical concentrations or activities of interest into electrical signals. These systems can be grouped into four major categories: reflection techniques; surface plasmon resonance; fibre optic techniques and integrated optic devices. Reflection teclmiques include ellipsometry, multiple integral reflection spectroscopy, and fluorescent capillary fill devices. Fibre-optic techniques include evanescent field fluorescence, optical fibre capillary tube, and fibre optic fluorescence sensors. Integrated optic devices include planer evanescent field fluorescence, input grading coupler immunosensor, Mach-Zehnder interferometer, Hartman interferometer and difference interferometer sensors. These examples of optical immunosensors are described in general in a review article by G. A. Robins (Advances in Biosensors), Vol. 1, pp. 229–256, 1991 More specific description of these devices are found for example in U.S. Pat. Pat. Nos. 4,810,658; 4,978,503; 5,186,897; R. A. Brady et al. (Phil. Trans. R. Soc. Land. B 316, 143–160, 1987) and G. A. Robinson et al. (in Sensors and Actuators, Elsevier, 1992).

In one embodiment of the present invention, cardiac myoglobin is detected in a sample of blood, serum or plasma, using the monoclonal antibody of the present invention, in a device comprising a filter membrane or solid support with a detection section and a capture section. The detector section contains an antibody (a detector antibody), which will react with the myoglobin. The detector antibody is reversibly immobilized onto the solid support and will migrate with the sample, when in use. It is preferred that the detector antibody is labelled, for example with a radionucleotide, an enzyme, a fluorescent moiety, luminescent moiety or a coloured label such as those described in the prior art, and discussed above. The capture section comprises a capture antibody, which is irreversibly immobilized onto the solid support. The antibodies, capture and detector antibody, and the necessary reagents are immobilized onto the solid support using standard art recognized techniques, as disclosed in the flow-through type immunoassay device discussed previously. In general, the antibodies are absorbed onto the solid supports as a result of hydrophobic interactions between non-polar protein substructures and non-polar support matrix material.

According to this embodiment of the present invention, if cardiac myoglobin is present in the sample, it will react with the detector antibody in the detector section and will migrate onto the alter membrane towards the capture section where the analyte will further bind with the capture antibody. Thus, the cardiac myoglobin will he sandwiched between the capture antibody and the detector antibody which contains a suitable label.

In this example of the present invention, if the detector antibody is labelled with a coloured label or an enzyme which will produce a coloured label, the patient's blood would first require centrifugation or some pre-filtering in order to remove the red blood cells so that the colour of the red blood cells will not interfere with the coloured labels. If radioactive labels or florescent labels pre to be used, a pre-filtration or centrifugation step may not be required. In this embodiment, the monoclonal antibody of the present invention is the capture antibody and the rabbit polyclonal antibody is the detector antibody, as in this embodiment the sample first contacts the detector antibody.

This immunoassay system is generally described in U.S. Pat. No. 5,290,675. The monoclonal antibody of this invention is particularly useful in this system because of its high affinity and specificity for cardiac myoglobin.

The following detailed examples will further illustrate the invention, which are not to he construed as limiting.

EXAMPLE

Example 1

Preparation of a Monoclonal Antibody Against Human Cardiac Myoglobin
Immunization Human cardiac myoglobin was purified from human heart ventricle according to the following procedure. The homogenate of human heart was subjected to an initial $(NH_4)_2SO_4$ precipitation (40%) followed by centrifugation at 6000 × g for 20 minutes at 4° C. The supernatant was precipitated further by 1M acetic acid, and the resulting supernatant collected after centrifugation at 12,000 × g (20 minutes, 4° C.). The pH of the supernatant was adjusted to pH 7.0 and further subjected to $(NH_4)_2SO_4$ fractionation (80% saturation). The resulting supernatant was then dialyzed against 50 mM phosphate-borate buffer, pH 8.0. The myoglobin was purified to a crude form by gel filtration on a Bio-Gel P-60 column (Bio-Rad, Hercules, Calif., Cat. #150–4160). The myoglobin was then further purified to homogeneity on a Affi-Blue Bio-Gel Affinity Column (Bio-Rad, Hercules, Calif., Cat. #153–7302).

Balb/c mice, a strain with $H-2^d$ haplotype from Charles River Canada, St. Constant, Quebec, Canada, female, 7–9 week old, were administered primary immunization of 50 μg of myoglobin in 1:1 mixture with Freund's Complete Adjuvant subcutaneously at the base of the neck. A secondary immunization was administered 4 weeks later consisting of an intra-peritoneal (i.p.) injection of 50 μg of myoglobin in a 1:1 mixture with Freund's Incomplete Adjuvant. This was followed by a tertiary i.p. boost of 100 μg of myoglobin in phosphate buffered saline (PBS pH 7.4), given 4 weeks later. Four days prior to fusion the mouse was administered an additional 100 μg of myoglobin in PBS pH 7.4, i.p. The mouse was sacrificed and the spleen removed.
Production of the Hybridomas and Antibodies The hybridoma cell line designated as 5Mb-64 was produced by the fusion of the immunocytes obtained from the spleen of immunized Balb/c mice with Sp2/0 murine myeloma cells as described by Fuller S. A., Takahashim; and Hurrell J. G. R., (Preparation of Monoclonal Antibodies; In Ausubel F., Brent R., Kingston R., et al., eds Current Protocols in Molecular Biology. New York: Greene Publishing Associates. 1987: Unit 11). The resulting fused cells were suspended in the HAT selection medium and plated onto 96-well plates which were pre-seeded with feeder cells, PFC (peritoneal exudate cells), as described by Fuller et al. (see above reference). Fresh HAT medium was added on day 7, and on day 9, 50% of the culture medium was removed and replaced with fresh MAT medium.

The hybridoma cultures were screened for the production of antibodies which are highly immunoactive to myoglobin. This was performed by the analysis of spent culture supernatants by Indirect Enzyme Linked Immunosorbent Assays. Polystyrene 96 well microtitre plates (Immunolon-4, Dynatech Labs, Chantilly, Va.) were coated with 2 μg/ml of human cardiac myoglobin in 100 mM Carbonate/Bicarbonate buffer, pH 9.6 overnight at 4° C. The excess binding sites were blocked by bovine serum albumin (BSA) in phosphate buffered saline (PBS), pH 7.2. The plates were then washed 4 times with PBS/0.05% Tween-20. The hybridoma culture supernatant was then added to the wells (100 μl) and incubated for 1 hour at 37° C. in a $CO_2$ incubator. The plates were then washed 4 times with PBS/Tween-20 (pH 7.2). The wells were then incubated with 100 μl of goat anti mouse IgG Fc-HRP (Jackson ImmunoResearch Lab, Inc., West Grove Penn.) at 0.5 μg/ml for 60 minutes at 37° C. The plates were washed 4 times with PBS/Tween-20 (pH 7.2). The substrate solution (0.5 mg/ml o-phenylenediamine, OPD (Sigma Chemicals, St. Louis Mo., and 0.03% $H_2O_2$ in 0.1M citrate-phosphate buffer, pH 5.0) was added at 100 μl/well and allowed to develop for 30 minutes in the dark. The reaction was then stopped using 25 μl of 4N $H_2SO_4$ solution/well. The plates were read at 490 nm on a BIORAD Microplate Reader (Bio-Rad, Hercules, Calif.).

Figure 1:
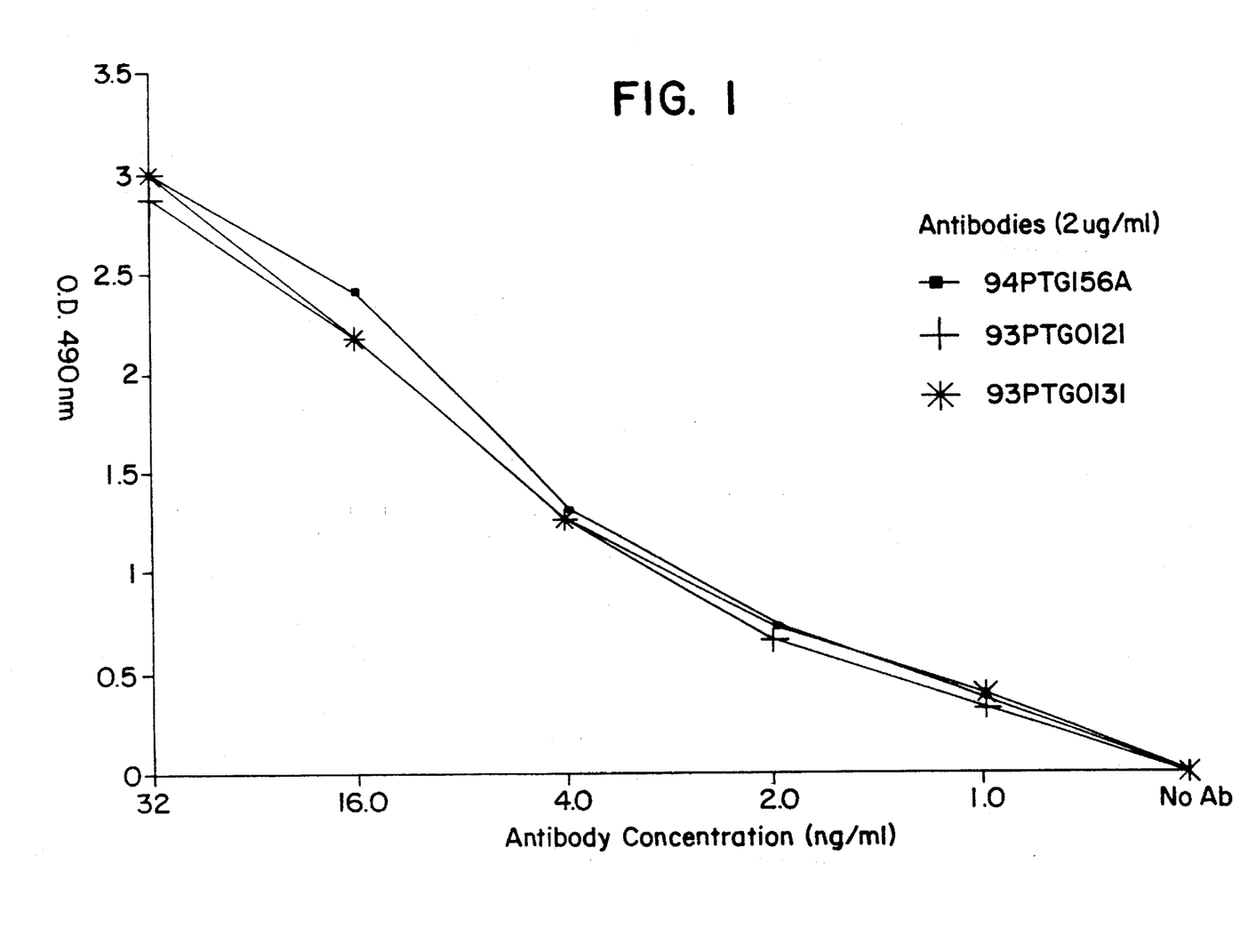
FIG. 1 shows the titration of three different purification lots of the 5Mb-64 antibody in a half sandwich assay in which myoglobin has been directly coated onto the polystyrene plates.
Figure 2:
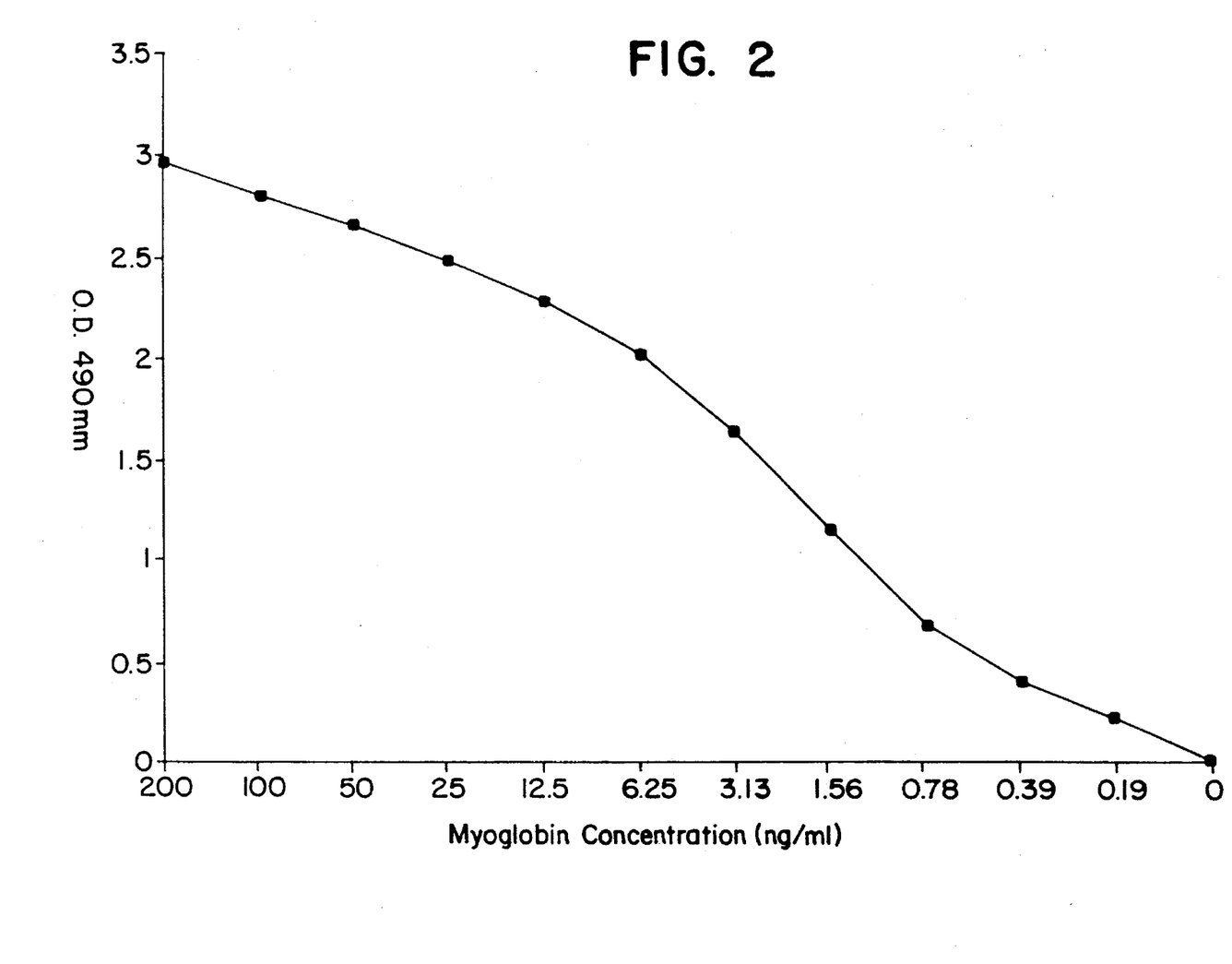
FIG. 2 shows the activity of the 5Mb-64 in a myoglobin immunoassay using rabbit anti-myoglobin antibodies as capture and 5Mb-64 as detector.

The specific cell line, 5Mb-64 (mouse #5, microtitre well #64) was isolated as it appeared to be an extremely immunoactive cell line exhibiting O.D. > 2.0 of culture supernatant assayed using the system described above. Immunoactivity remained high repeatedly and consistently in the various stages of cloning and screening. For example, FIG. 1 shows the titration of three different purification lots of the 5Mb-64 antibody in a half sandwich assay in which myoglobin has been directly coated onto the polystyrene plates. This cell line was also tested in a full sandwich ELISA assay, using a rabbit polyclonal antibody as the antigen capture (immobilized or anchor antibody) and 5Mb-64 as the antigen detector (labelled or tag antibody) and visa versa when 5Mb-54 was used as a capture antibody in this assay, no activity was observed and as such no binding of myoglobin was recorded. However, when the antibodies were reversed, i.e. rabbit polyclonal antibody capture and 5Mb-64 detector sensitivities of less than 0.5 ng/ml were achieved, FIG. 2. This hybridoma cell line was deposited with the American Type Culture Collection on Aug. 25, 1994 under Accession Number HB 11708.

Bald/c mice, as described A hove, previously treated with 0.5 ml of pristance were injected intraperitoneally with 1–5×10⁶ cloned hybridoma cells in 0.5 ml phosphate buffered saline (PBS), pH 7.4. Approxlmately 2 weeks later, ascites were collected and the monoclonal antibody was affinity purified on a Protein A or Protein C column, using known procedures. The purified monoclonal antibody of the present invention was then used for various immunochemical studies.

Some properties, as determined using the methods described in Fuller et al. (set above), of the 5Mb-64 Hybridoma Cell Line are as follows:

(1) cell doubling–time 12.06 hours (2) average ml ascites produced ranging from 3–5 ml/mouse (3) average yield of antibody–1.2 mg/ml ascites (4) stability-greater than 25 passages

Example 2

Phystcochemical Characterization
Antibody Class and Subclass

Antibody class and subclass were determined by ELISA with a commercial assay kit (Bio-Rad, Hercules Calif., Cat #172–2055), using the method described by the manufacture. The cell line 5Mb-64 was determined by this assay system to be of the IgGl, K isotype.

Isoelectric Point (pI)

Isoelectric point determination was performed using the Model III Mini IEF cell (Bio-Rad, Hercules Calif. Cat. #170–2975) following the instructions provided by the manufacturer. The pI value for cell line 5Mb64 was determined to be, 6.6.

Kinetics and Affinity Constant

A) Association Rate Constant (ka)

The association rate or the rate at which a monoclonal and its antigen bind can be determined utilizing the binding curve generated on the BIAcore. The system uses surface plasmon resonance which detects changes in optical properties at the surface of a thin gold film on a glass support. Detailed theoretical background and procedures are described by R. Karlsson, et. al. (J. Immunol Methods, 145, 229, 1991).

Kinetic nins were performed as follows. The monoclonal antibody at a constant concentration of 30 µg/ml in 10 mM Hepes, 0.15 M NaCl, 3.4 mM ethylenediaminetetraacetic acid disodium salt, 0.05% surfactant 20 (HISS, pH 7.4) was allowed to interact with sensor surfaces on which rabbit and-mouse $IgG_{Pc}$ (Jackson ImmunoRescarch Lab, Inc.) had been immobilized. The antigen, myoglobin, at concentrations ranging from 125 µg/ml to 20 µg/ml, was allowed to interact with the bound monoclonal antibody. The runs were performed at 25° C., at a flow rate of 5 µl/mm during 6 min. (30 µl injection), taking a total of 24 report points. After injection of the antigen was complete, dissociation of the antigen from the antibody was monitored by taking a total of 18 report points. After the run, the surface was regenerated by injecting a 1 M formic acid solution during 1 mm. (5 µl injection). The instrument software produces a table of $dR_A/dt$ and $R_A$ values that can be directly used in a plotting program (Microsoft Excel). By plotting the graph dR/dt vs R a five different concentration of antigen and subsequently plotting the slopes of these lines vs the concentration of antigen, the slope of this second graph is the association rate constant ka $(M^{-1}, s^{-1})$.

Where:
dR/dt is the rate of formation of antigen antibody complexes i.e. the derivative of the binding curve; and R is the antigen/antibody complex as measured by the BIAcore in resonance units.

B) Dissociation Rate Constant (kd)

The dissociation rate or the rate at which a monoclonal and its antigen release can be determined utilizing the dissociation curve generated on the BIAcore. By plotting and determining the slope of the log of the drop in response vs time curve one can measure the dissociation rate constant kd $(s^{-1})$.

C) Affinity or Equilibrium Constant (Ka or Kd)

The affinity or equilibrium constants is the ratio of the association and dissociation rate constants.

Where;
Ka=ka/kd
Kd=kd/ka

Figure 3:
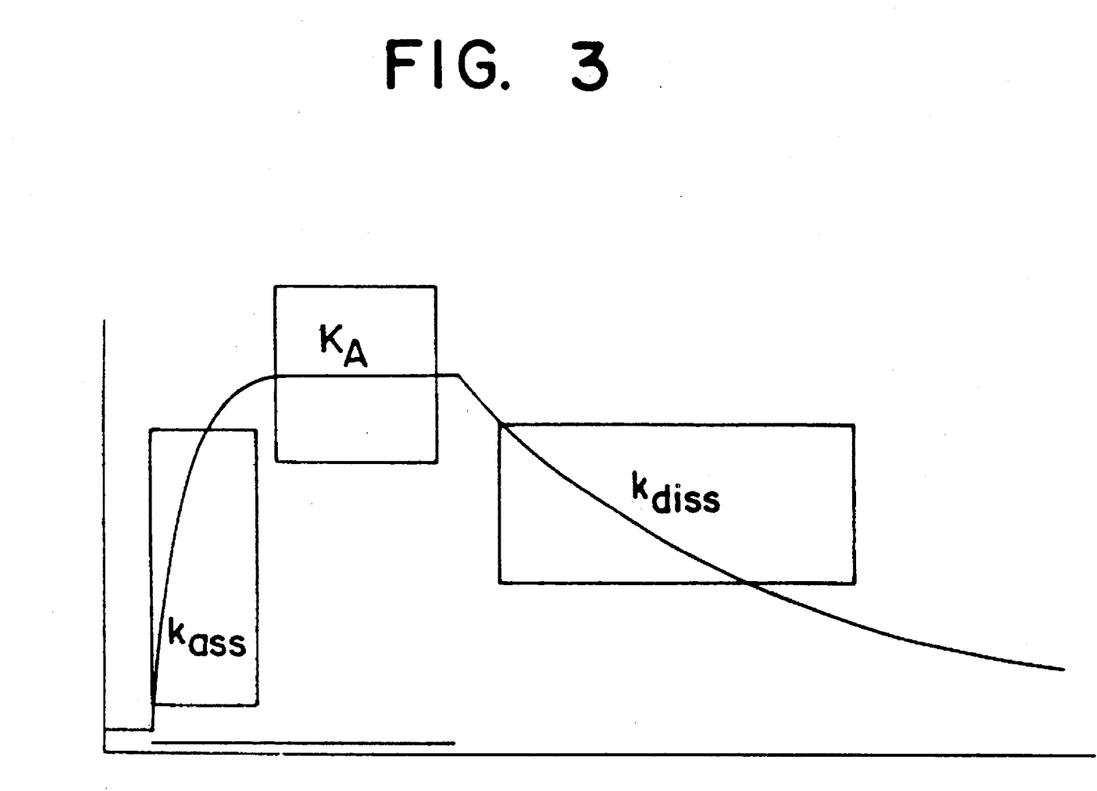
FIG. 3 shows a prior art association/dissociation curve using BIAcore.

A typical curve of association and dissociation is shown in FIG. 3.

Affinity constants were determined in two ways. The experiment was conducted using the antigen alone and also using the antigen bound to a rabbit anti-myoglobin polyclonal antibody. These results are shown in Table 1.

TABLE 1

| | Affinity Constants | |
| --- | --- | --- |
| | 5Mb-64 (Ag* only) | 5Mb-64 (Polyclonal** & Ag) |
| ka (on rate) | not measurable | 6.19 10³ $M^{-1}s^{-1}$ |
| kd (off rate) | not measurable | 2.09 10⁻³ $s^{-1}$ |
| Ka (affinity constant) | not measurable | 3.01 10⁶ $M^{-1}$ |
| Kd (affinity constant) | not measurable | 3.33 10⁻⁷ M |

*Human cardiac myoglobin
**Rabbit anti-myoglobin polyclonal antibody

As discussed previously, no binding is observed when the monoclonal antibody of the present invention is tested directly against bound myoglobin However binding does occur when the monoclonal antibody of the present invention is tested against myoglobin that has already been bound to a rabbit polyconal antibody.

Example 3

Antigenic Specificity

Figure 4A:
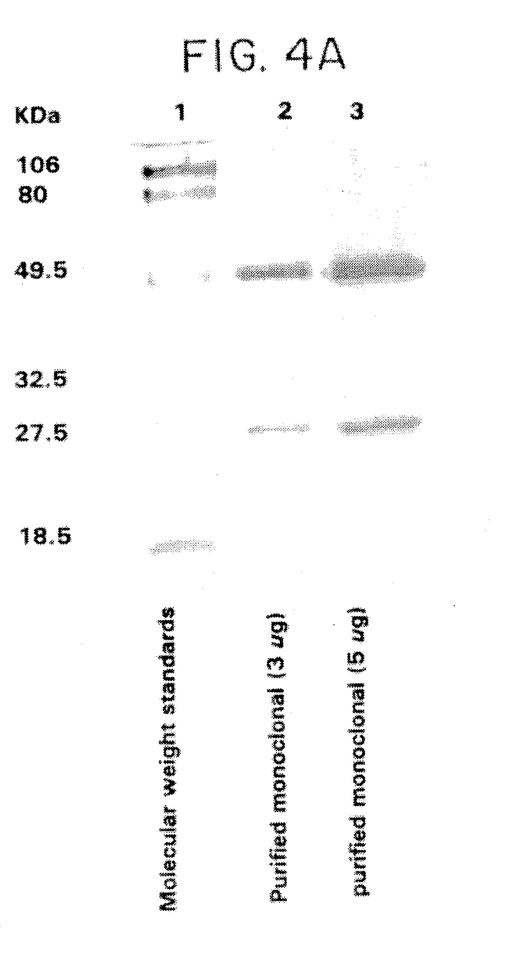
FIG. 4 (a) is a SDS-PAGE gel of myoglobin and a corresponding immunoblot (c) with 5Mb-64 showing the immunospecificity myoglobin, (b) pI value of 6.6 determined by isoelectric focusing.
Figure 4B:
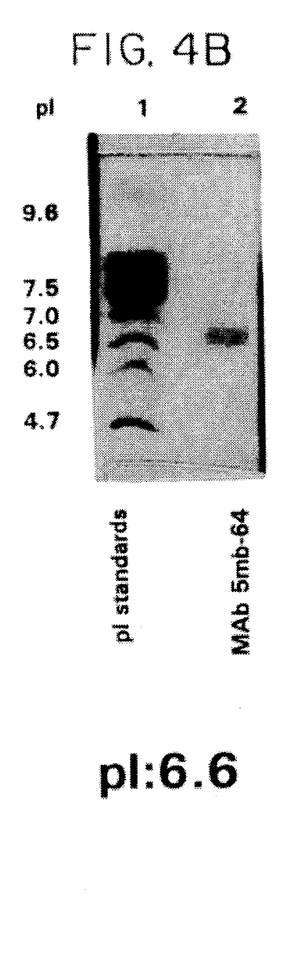
Figure 4C:
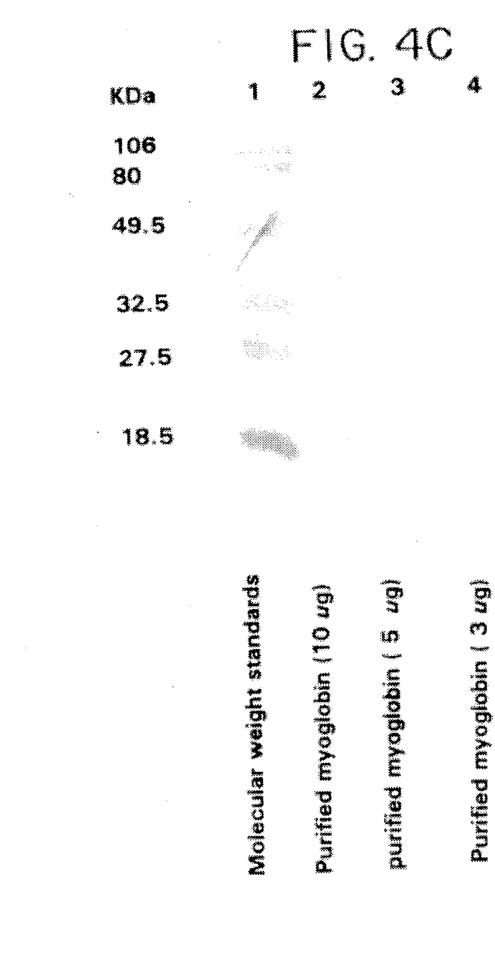

The specificity of the 5Mb-64 antibody was assessed by immunoblot, using methods well known in the an, as described for example in Tsang, V.C.W. et al. Methods in Enzymol. Vol. 92, 377, 1983. Purified human cardiac myoglobin was electrophoresed on a SDS-PAGE gel and transferred to nitrocellulose. The nitrocellulose was incubated in a solution of 5% skim milk in Tris buffered saline with Tween-20 (TTBS), pH 7.5, in order to block any non-specific binding. This was followed by incubation of 1 to 10 μg/ml of the 5Mb-64 monoclonal in TTBS for 1 hour. The nitrocellulose was washed in TTBS, pH 7.4, and incubated with horseradish peroxidase (HRP) labelled goat anti-mouse IgG (Bio-Rad, Hercules, Calif., Cat #170–6516). The HRP bound antibody was visualized by the incubation in 4-chloro-1-naphthol colour development reagent, as described previously. The colour development was stopped by washing in distilled water. The immunoblot is shown in FIG. 4. This clearly indicates the immunospecificitry of 5Mb-64 to the single protein band of myoglobin.

Figure 5:
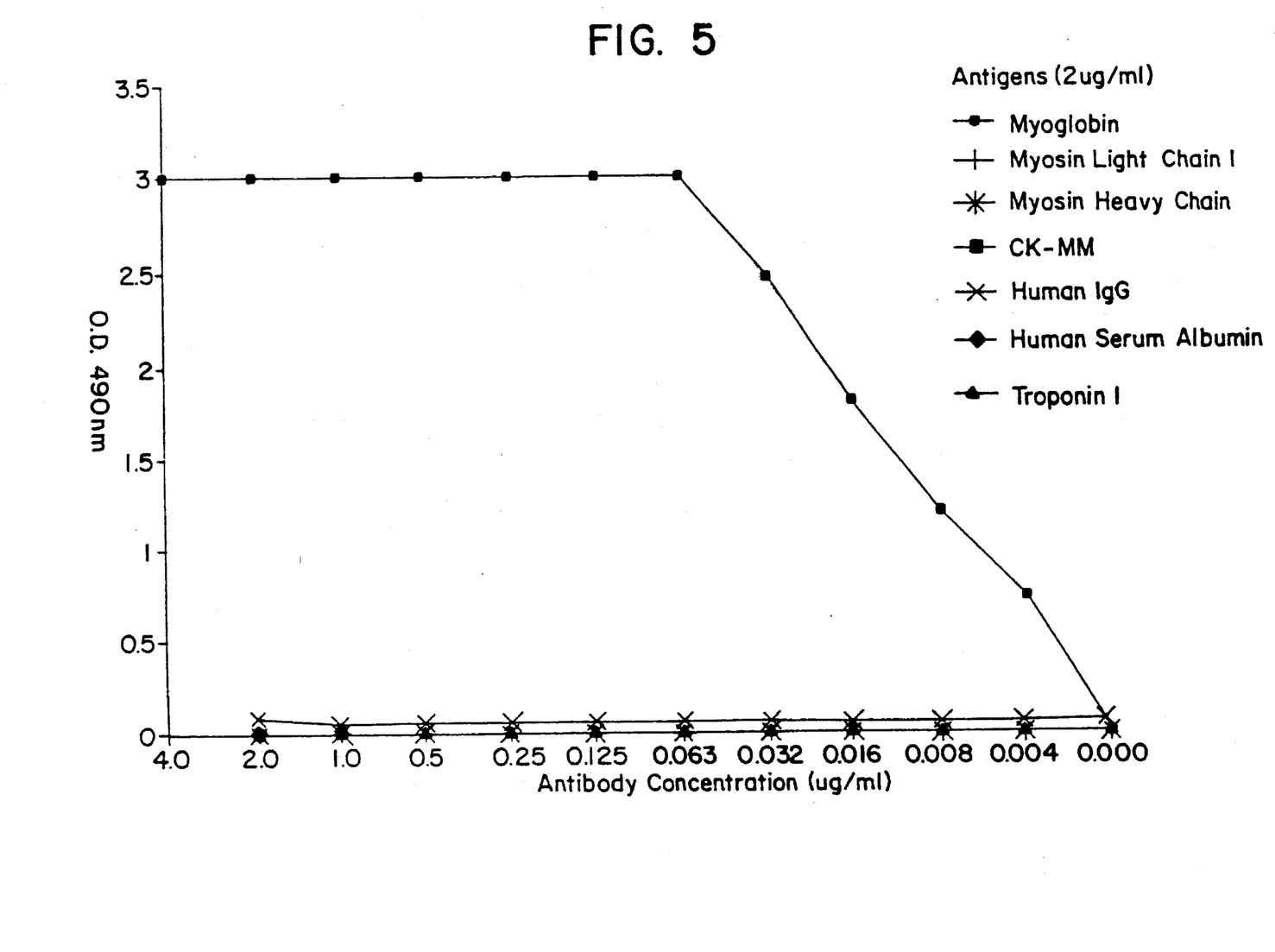
FIG. 5 shows the lack of cross reactivity of the 5Mb-64 antibody with a panel of cardiac and non-cardiac proteins.

In order to further confirm the specificity of 5Mb-64, this antibody was used in a solid phase ELISA test with a panel of cardiac and non-cardiac proteins. These proteins were coated onto polystyrene ELISA plates at 2 μg/ml, as described previously. The monoclonal antibody was tested against these antigens at a concentration ranging from 4 μg/ml to 0.004 μg/ml, with the concentration dropping in 50% steps. The bound antibody was detected by a goat anti-mouse Fc antibody (Jackson ImmunoResearch Lab, Inc.) at 0.5 μg/ml and visualized using the OPD substrate, as described previously. The results are shown in FIG. 5. The monoclonal antibody 5Mb-64 shows no cross reactivity with any of the protein tested, except for myoglobin.

Example 4

Detection of Cardiac Myoglobin in a Biological Sample

Figure 6:
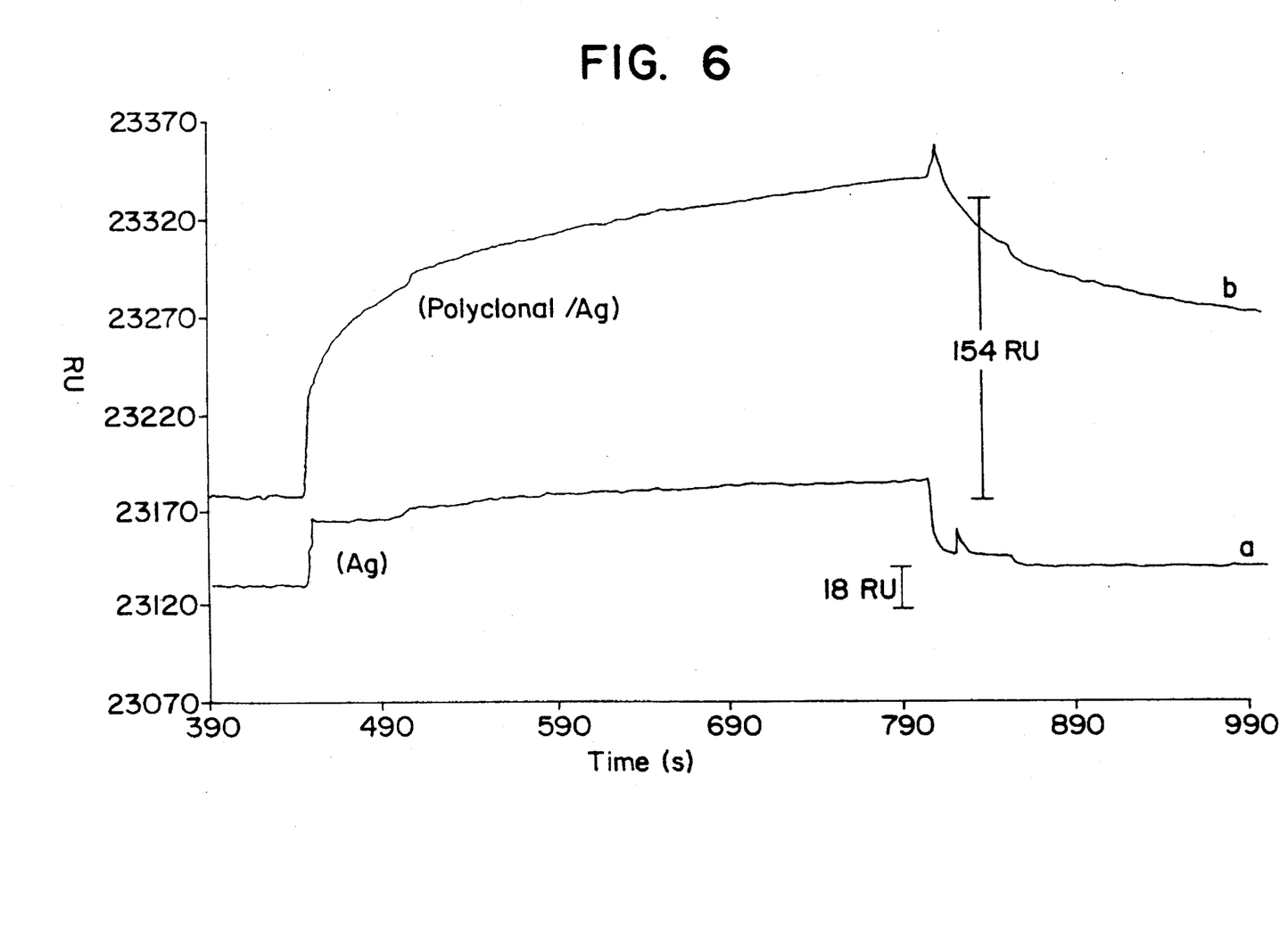
FIG. 6 is a BLAcore profile showing (a) the association of 5Mb-64 with myoglobin only the antibody binding only 18 RUs of antigen, and (b) the enhanced activity of 5Mb-64 (154 RUs) when the antibody is presented with Mb bound to rabbit polyclonal antibody prior to the presentation to 5Mb-64.

As the normal levels of myoglobin in the blood, serum or plasma can be as high as 70 ng/m, the present assay has been optimized to detect serum myoglobin levels of 80 ng/ml or greater. This has been achieved by the use of a rabbit polyclonal antibody as the detector antibody and 5Mb-64 as the capture antibody. The 5Mb-64 monoclonal antibody displays the unique capability of recognizing myoglobin most effectively when myoglobin has been bound by another antibody. Using the BIAcore system, as described previously, it is possible to observe this interaction quite clearly. When the 5Mb-64 monoclonal antibody was covalently bound to the sensor chip and free human cardiac myoglobin was introduced, very little (18 RU) antigen binding was observed. But, when the antibody was presented with myoglobin which had been premixed with rabbit polyclonal antibody the antigen association was increased by more than 5 fold. Thus, it appears that 5Md-64recognizes an epitope of the myoglobin molecule that is Only exposed as a result of having undergone a conformational change resulting from the binding to another molecule, for example, another antibody. (See FIG. 6).

Furthermore, an analysis of the binding kinetics and determination of the affinity constant (Table 1) shows that 5Mb-64 has such a low affinity for free myoglobin that it could not be measured. The affinity of 5Mb-64 to the exposed epitope of antibody-bound-myoglobin was $3.01 \times 10^6$ $M^{-1}$.

Extensive pairwise experiments with a panel of monoclonal and polyclonal antibodies, has shown that the most sensitive pair of antibodies which achieved optimal sensitivity, specificity and time requirements (i.e., 2–3 seconds) were the anti-myoglobin rabbit polyclonal antibody and 5Mb-64. Accordingly, 5Mb-64 recognizes an epitope or antigenic determinant on the myoglobin milecule only exposed as a result of a conformational change arising from the binding of the myoglobin to another molecule, for example, the anti-myoglobin rabbit polyclonal antibody. The immunoactivity of the 5Mb-64 antibody is dramatically enhanced by this conformational change.

In this example, the monoclonal antibody produced from hybridoma cell line 5Mb-64 was used as a capture antibody in a flow through assay system, based on the double antibody sandwich assay.

A sample of a patient's serum (50 μl to 150 μl) was added to the assay system through a sample opening, which was in fluid communication with a reagent pad containing the labelled anti-myoglobin rabbit polyclonal detect or antibody. If the sample size was small a carrier fluid was added after the application of the sample. The carrier fluid can be any buffer solution; for example phosphatic buffer, saline. Tris-HCI or water. If the sample, contained cardiac myoglobin it will bind to the detector antibody in the reagent pad. The detector antibody was reversibly immobilized and thus migratible with the sample. The sample continued to flow from the reagent pad onto a filter membrane, onto which the monoclonal antibody of the present invention was irreversible immobilized (capture antibody). Labelled detector antibody-cardiac myoglobin complex, if present, will bind to the capture antibody on the filter membrane. The presence of the analyte, which has been labelled with the labelled detector antibody, will thus be positioned at the location of the capture antibody, which generally coincide in position to a display window in the assay system.

All references cited herein tire specifically incorporated by reference.

Although the disclosure describes and illustrates preferred embodiments of the invention, it is to he understood that the invention is not limited to these particular embodiments. Many variations and modification will now occur to those skilled in the art. For a definition of the invention, reference is made to the appended claims.

We claim:

1. Hybridoma cell line 5Mb-64, deposited with the American Type Culture Collection under Accession Number HB 11708.

2. A monoclonal antibody produced by hybridoma cell line 5Mb-64, deposited with American type Culture Collection under Accession Number HB 11708.

3. A method of detecting myoglobin in a sample using a monoclonal antibody produced by hybridoma cell line 5Mb-64, deposited with American Type Culture Collection under Accession Number HB 11708, which comprises contacting the sample with an anti-myoglobin polyclonal antibody, to produce a polyclonal antibody-myoglobin complex; contacting the complex with the monoclonal antibody to produce a polyclonal antibody-myoglobin-monoclonal antibody complex, wherein the monoclonal antibody is irreversibly immobilized on a solid phase support; and detecting the polyclonal antibody-myoglobin-monoclonal antibody complex.

4. The method according to claim 3 wherein the polyclonal antibody is a rabbit polyclonal antibody.

* * * * *

UNITED STATES PATENT AND TRADEMARK OFFICE
CERTIFICATE OF CORRECTION

PATENT NO. : 5,573,957　　　　　　　　　　　　　　　　　　　Page 1 of 5
DATED : November 12, 1996
INVENTOR(S) : Beatrice Cardone et al It is certified that error appears in the above-indentified patent and that said Letters Patent is hereby corrected as shown below:

In Column 1, line 24, "lieme" should read --heme--,　　　　　　　　　　and line 59, "increased" should read --increase--,     In Column 2, line 8, "Bllis" should read --Ellis--,     In Column 3, lines 7 and 13, "5Mb64" should read --5Mb-64--,     line 29, "5Mb-64in" should read --5Mb-64 in--,     line 31, "5Mb-64as" should read --5Mb-64 as--,     line 42, "only the" should read --only, the--, and     line 67, "or" should read --of--,     In Column 4, line 36, "Injected" should read --injected--,     line 41, "rear" should read --ear--;

UNITED STATES PATENT AND TRADEMARK OFFICE
CERTIFICATE OF CORRECTION

PATENT NO. : 5,573,957   Page 2 of 5
DATED : November 12, 1996
INVENTOR(S) : Beatrice Cardone et al It is certified that error appears in the above-indentified patent and that said Letters Patent is hereby corrected as shown below:

line 42, "trappings" should read --tappings--, and       line 55, "Analysts" should read --Analysis--,       In Column 5, line 44, "sing" should read --using--,       In Column 6, line 15, "Rasie" should read --Basic--,       line 17, "Systems" should read --systems--,       line 21, "ofthe" should read --of the--,       line 42, "And" should read --and--,       line 43, "or" should read --of--,       line 64, "Au" should read --An--,       In Column 7, line 11, "In" should read --an--,       line 17, "sole" should read --sol-- ;

line 56, "rube" should read --tube--, line 59, "bends" should read --beads--, line 67, "IMC™" should read --IMX™--,

UNITED STATES PATENT AND TRADEMARK OFFICE
CERTIFICATE OF CORRECTION

PATENT NO. : 5,573,957
DATED : November 12, 1996
INVENTOR(S) : Beatrice Cardone et al It is certified that error appears in the above-indentified patent and that said Letters Patent is hereby corrected as shown below:

In Column 8, line 4, "say" should read --assay--, line 11, "array" should read --assay--, line 21, "say" should be deleted , line 44, "Systems" should read --systems--, and line 64, "Pat." should appear only once ,

In Column 9, line 38, "pre" should read --are--, and line 45, "5,290,675" should read --5,290,678,

In Column 10, line 24, "Takahashim" should read --Takahashi M.,--.

line 34, "MAT" should read --HAT--,

In Column 11, line 14, "Bald/C" should read --Balb/C--,

UNITED STATES PATENT AND TRADEMARK OFFICE
CERTIFICATE OF CORRECTION

PATENT NO. : 5,573,957     Page 4 of 5
DATED     : November 12, 1996
INVENTOR(S) : Beatrice Cardone et al It is certified that error appears in the above-indentified patent and that said Letters Patent is hereby corrected as shown below:

line 14, "A hove" should read --above--, line 15, "pristance" should read --pristane--, line 35, "Phystochemical" should read --Physiochemical--, line 46, "5Mb64" should read --5Mb-64--, line 58, "nins" should read --runs--, line 61, "HISS" should read --HBS--, line 63, "$IgG_{Pc}$" should read --$IgG_{Fc}$--, line 65, "125" should read --1.25--, In Column 12, line 5, "mm" should read --min--, line 9, "R a five" should read --R at five--, and line 63, "the an" should read --the art--, In Column 13, line 32, "ng/m" should read --ng/ml--, line 47, "5Md-64recognizes" should read --5Mb-64 recognizes--,

UNITED STATES PATENT AND TRADEMARK OFFICE
CERTIFICATE OF CORRECTION

PATENT NO. : 5,573,957
DATED : November 12, 1996
INVENTOR(S) : Beatrice Cardone et al It is certified that error appears in the above-indentified patent and that said Letters Patent is hereby corrected as shown below:

line 48, "Only" should read --only--,

In Column 14, line 2, "milecule" should read --molecule--, line 16, "detect or" should read --detector--, line 19, "phosphatic" should read --phosphate--, and "saline. Tris-HCL" should read --saline, Tris-HCL--, line 31, "coincide" should read --conicides--, and line 33, "tire" should read --are--.

Signed and Sealed this

Twelfth Day of May, 1998

Attest:

BRUCE LEHMAN

Attesting Officer

Commissioner of Patents and Trademarks